US010394057B2

(12) United States Patent
Starner et al.

(10) Patent No.: US 10,394,057 B2
(45) Date of Patent: Aug. 27, 2019

(54) EYES CLOSED INTERFACE

(71) Applicant: Verily Life Sciences LLC, Mountain View, CA (US)

(72) Inventors: Thad Eugene Starner, Atlanta, GA (US); Michael Patrick Johnson, Sunnyvale, CA (US); Brian Otis, Saratoga, CA (US); Max Benjamin Braun, San Francisco, CA (US); Nathan Pletcher, Mountain View, CA (US); Joshua N. Haddock, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 35 days.

(21) Appl. No.: 15/425,140

(22) Filed: Feb. 6, 2017

(65) Prior Publication Data

US 2017/0227792 A1 Aug. 10, 2017

Related U.S. Application Data

(60) Provisional application No. 62/292,489, filed on Feb. 8, 2016.

(51) Int. Cl.
*G02C 7/04* (2006.01)
*G02C 11/00* (2006.01)
(Continued)

(52) U.S. Cl.
CPC ............... *G02C 11/10* (2013.01); *A61B 3/10* (2013.01); *A61B 3/113* (2013.01); *A61B 5/0002* (2013.01);
(Continued)

(58) Field of Classification Search
CPC ............ A61B 2562/028; A61B 5/0002; A61B 5/1103; A61B 5/14532; A61B 5/1477;
(Continued)

(56) References Cited

U.S. PATENT DOCUMENTS 6,163,281 A * 12/2000 Torch .................. A61B 3/0066
340/575
9,072,465 B2 7/2015 Pugh et al.
(Continued)

FOREIGN PATENT DOCUMENTS

EP 2772789 A1 9/2014
EP 3125021 A1 2/2017
(Continued)

OTHER PUBLICATIONS

PCT/US2017/016850—International Search Report and Written Opinion dated May 11, 2017, 9 pages.

*Primary Examiner* — William R Alexander
(74) *Attorney, Agent, or Firm* — Christensen O'Connor Johnson Kindness PLLC

(57) ABSTRACT

An eye-mountable device including a lens including a polymeric material, the lens operable to be removably mounted over a corneal surface of an eye and to be compatible with a motion of an eyelid when the concave surface is so mounted; a sensor coupled to the lens and operable to provide output data indicative of whether an eyelid of an eye on which the lens is mounted is closed; and a display operable to display a light signal in response to the output data from the sensor that the eyelid is closed. A method including determining whether an eyelid of a wearer of an eye-mountable device is closed; and when an eyelid of a wearer is closed, sending a light signal from the eye-mountable device.

21 Claims, 6 Drawing Sheets

(51) Int. Cl.
*G02C 11/04* (2006.01)
*A61B 3/113* (2006.01)
*G02C 7/08* (2006.01)
*A61B 5/145* (2006.01)
*A61B 5/00* (2006.01)
*A61B 3/10* (2006.01)
*A61B 5/11* (2006.01)
*A61B 5/1477* (2006.01)

(52) U.S. Cl.
CPC .......... *A61B 5/1103* (2013.01); *A61B 5/1477* (2013.01); *A61B 5/14532* (2013.01); *A61B 5/6821* (2013.01); *G02C 7/04* (2013.01); *G02C 7/049* (2013.01); *G02C 7/081* (2013.01); *G02C 11/04* (2013.01); *A61B 5/742* (2013.01); *A61B 2562/028* (2013.01)

(58) Field of Classification Search
CPC ....... A61B 5/6821; A61B 5/742; G02C 11/10; G02C 11/00; G02C 11/04; G02C 7/04; G02C 7/049; G02C 7/081
USPC .......................................... 351/158
See application file for complete search history.

(56) References Cited

U.S. PATENT DOCUMENTS

| | | | |
|---|---|---|---|
| 10,101,581 B2* | 10/2018 | Pugh | A61B 5/4809 |
| 2002/0049389 A1* | 4/2002 | Abreu | A61B 3/1241 |
| | | | 600/558 |
| 2012/0140167 A1 | 6/2012 | Blum | |
| 2014/0081178 A1* | 3/2014 | Pletcher | G02C 7/04 |
| | | | 600/595 |
| 2014/0118829 A1 | 5/2014 | Ma et al. | |
| 2014/0240655 A1 | 8/2014 | Pugh et al. | |
| 2015/0005750 A1* | 1/2015 | Kelleher | A61F 9/00802 |
| | | | 606/3 |
| 2015/0061999 A1 | 3/2015 | Kim et al. | |
| 2017/0031159 A1* | 2/2017 | Pugh | A61B 5/4809 |
| 2017/0092235 A1* | 3/2017 | Osman | G06F 3/012 |
| 2017/0112433 A1* | 4/2017 | Pugh | G02C 7/04 |
| 2018/0035882 A1* | 2/2018 | Gutierrez | A61B 3/101 |
| 2018/0217402 A1* | 8/2018 | Larmagnac | G02B 3/14 |

FOREIGN PATENT DOCUMENTS

| | | |
|---|---|---|
| WO | 2015/191241 A1 | 12/2015 |
| WO | 2015/194120 A1 | 12/2017 |

* cited by examiner

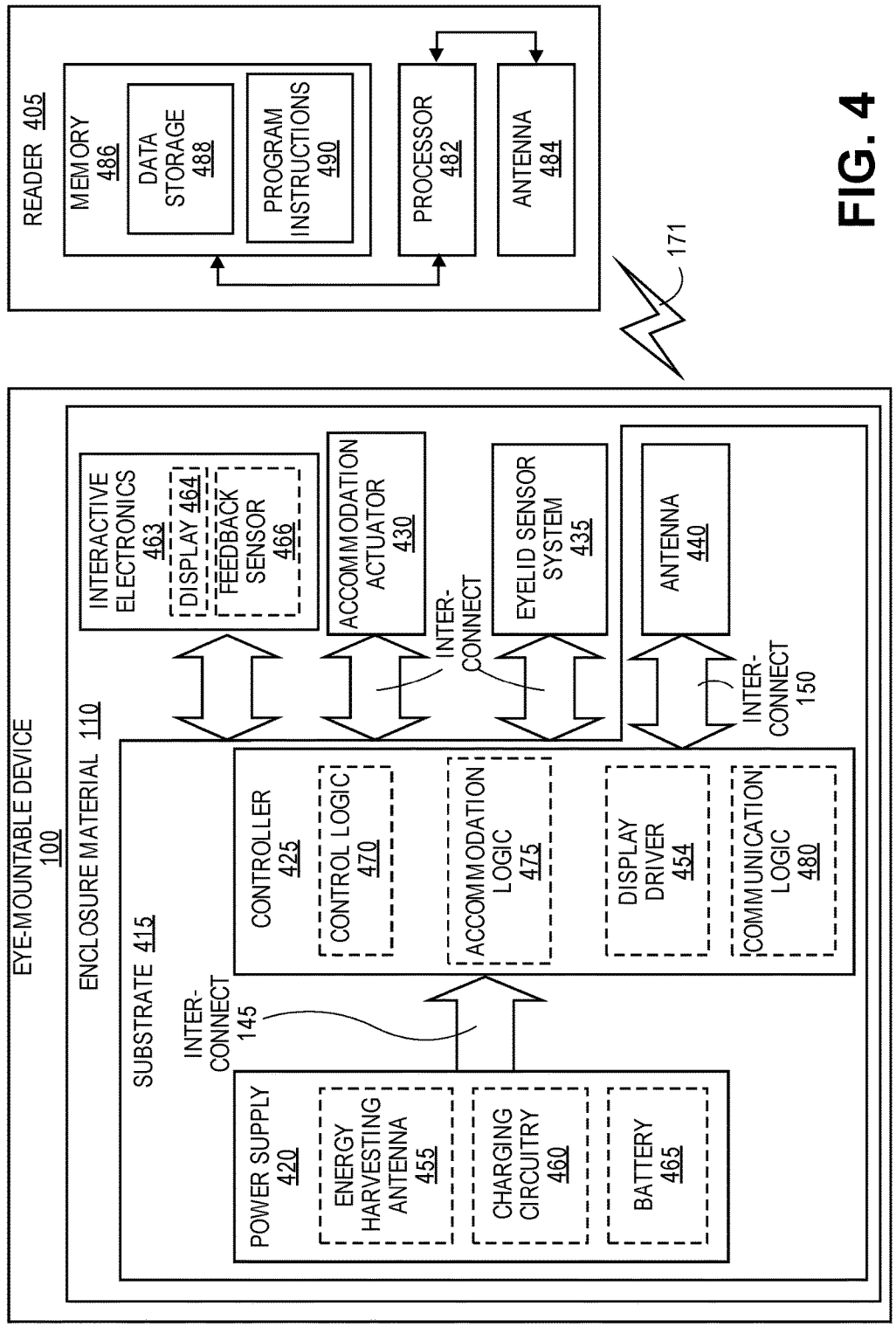

EYES CLOSED INTERFACE

CROSS-REFERENCE TO RELATED APPLICATION

The application is a non-provisional application which claims the benefit of the earlier filing date of U.S. Provisional Application No. 62/292,489, filed Feb. 8, 2016 and incorporated herein by reference.

TECHNICAL FIELD

Optics and contact devices.

BACKGROUND INFORMATION

Smart eye contact devices or eye mountable devices that incorporate a processor and miniaturized technology offer unique opportunities for health monitoring and enhancement. Representative of the benefits of smart eye contact devices include the ability to diagnose and/or monitor disease states, provide drug delivery, employ reality augmentation, improve or adjust focus or accommodation and provide night vision.

SUMMARY

In one embodiment, an ophthalmic sensing platform or eye-mountable device includes a sensor operable to determine when an eyelid is closed, a display operable to display a light signal in response to a signal from the sensor that the eyelid is closed, and control electronics situated on a substrate connected to a lens including a body of a polymeric material formed to be contact mounted to an eye. In one embodiment, an eye-mountable device also includes a sensor system such as a sensor system to diagnose or monitor a bodily condition or improve or adjust focus or accommodation. The control electronics are operable to receive information from the sensor system and send a light signal regarding the information to a wearer of the eye-mountable device when an eyelid is closed.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIG. 4 is a functional block diagram of an embodiment of an eye-mountable device including an accommodating lens with a tear film sensor system for determining whether an eyelid is open or closed and to display a signal when the eyelid is closed, in accordance with an embodiment of the disclosure.

DETAILED DESCRIPTION

Figure 1:
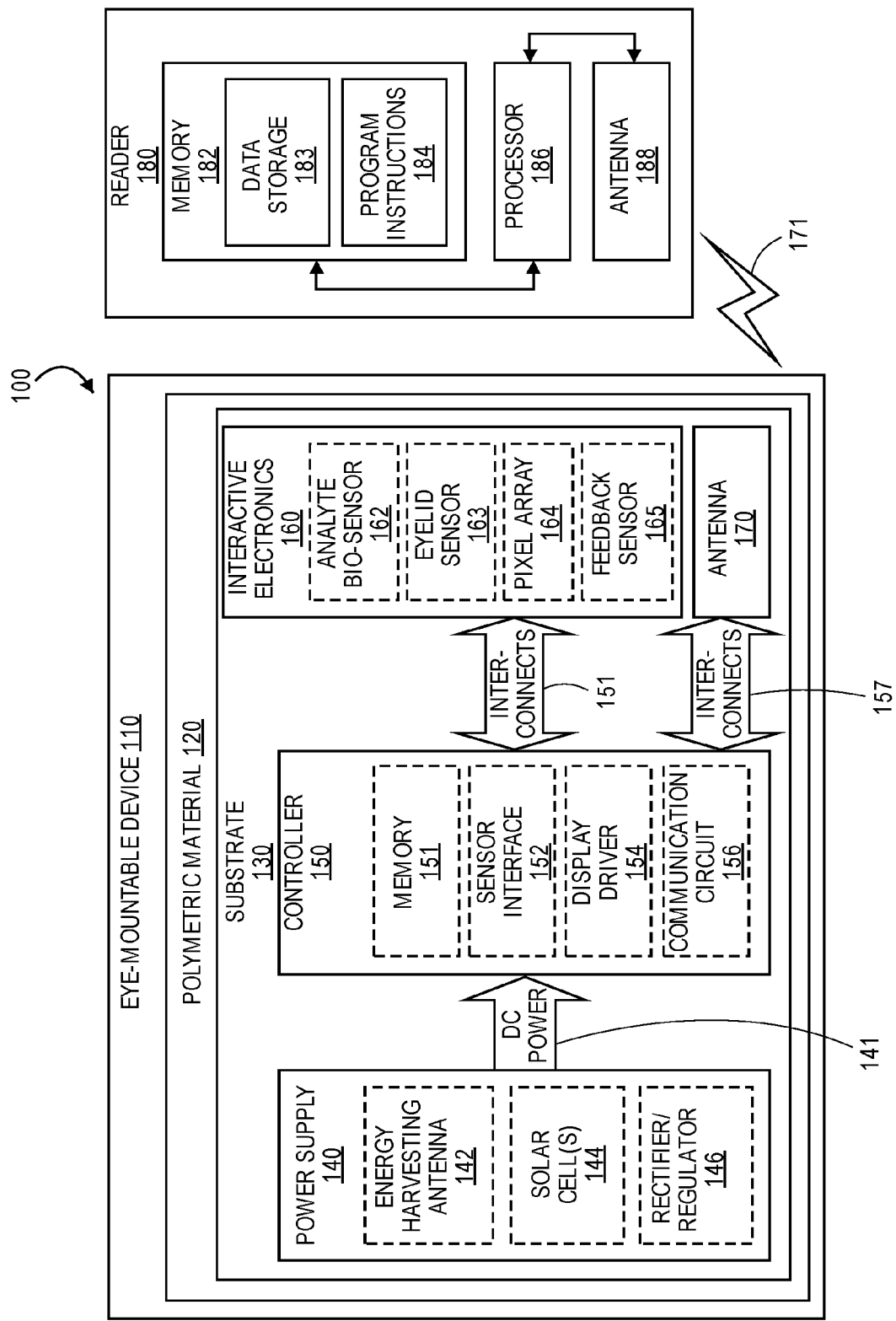
FIG. 1 is a functional block diagram of an embodiment of an eye-mountable device with bodily sensing functionality to monitor a condition of a wearer of the device, an eyelid sensor to determine when an eyelid is closed and a display to display a signal when the eyelid is closed.

Embodiments of an apparatus, system and methods of forming a contact device or eye-mountable device are described herein. In the following description numerous specific details are set forth to provide an understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described herein is an eye contact device or eye-mountable device that includes circuitry that is operable to signal to a wearer of the device when an eyelid of the wearer is closed. A representative signal includes a light signal (e.g., a point, points of light, or alphanumeric characters). Embodiments of an eye contact device or an eye-mountable device may include power supply circuitry, control electronics, accessory devices (e.g., an accommodation actuator), a sensor system (e.g., a chemical sensor system, a capacitive sensor system), and an optional antenna all embedded within an enclosure material formed to be contact mounted to an eye. With respect to signaling a wearer of the eye contact device, the device also includes an eyelid sensor operable to determine when an eyelid of an eye on which the device is mounted (worn) is closed and a display operable to display the signal to the wearer in response to a signal from the eyelid sensor that the eyelid is closed.

With regard to the components of an eye-mountable device or eye contact device, control electronics, in one embodiment, are representatively connected to monitor a bodily condition. An example of a bodily condition is a blood glucose level. Information about blood glucose levels is particularly useful for people with diabetes. To monitor a blood glucose level, an eye-mountable device includes a chemical sensor system (e.g., an electrochemical sensor system) to sense blood glucose levels of a wearer of the device. In one embodiment, if the chemical sensor system determines that a blood glucose level is above or below an acceptable threshold, the control electronics will notify the wearer of the device. In one embodiment, the control electronics will determine when an eyelid of the wearer is closed (e.g., a blink or intentional closure). The device includes an eyelid sensor, such as a sensor operable to detect a light change (e.g., a photocell), a movement of the eye contact device (e.g., an accelerometer) or an impedance of a current in tear film. When it is determined that an eyelid is closed by, for example, a signal from the eyelid sensor, the control electronics will send a light signal to the wearer on a display. The light signal, in one embodiment, is a point of light or points of light. In one embodiment, the point or points of light is one color when a blood glucose level is higher than a threshold value and another color when a blood glucose level is lower than a threshold value. In another embodiment, the light signal is one or more alphanumeric characters indicating, for example, a level above or below a threshold.

As described above, the eye mountable device or eye contact device is operable to display a light signal when an eyelid is closed. Once the eyelid is determined to be closed, the display of the device is illuminated with a light signal, whether it be a point or points of light or alphanumeric characters. While the eyelid may not block out all ambient light, the lit display against the relatively uniform background of the eyelid will provide a high contrast image with no distracting other features in the field of view of the wearer. If the wearer has closed his or her eyelids involuntarily (which happens on average 15-20 times per minute), the wearer might notice the display, even as an after image. The wearer can then close his or her eyes or rapidly blink them to better examine the display. In one embodiment, where an eyelid sensor of the device recognizes that the wearer is keeping his or her eyes closed for a period longer than a blink, control circuitry of the device uses such recognition to present more detailed information, such as in a serial fashion (e.g., one light signal after another). For example, different signals can be encoded in the pattern, color and sequence of simple blinking light signals (e.g., red: blood glucose high, flashing four times indicates a 4 on a scale of 5). In another embodiment, a display uses diffraction pattern generators and laser diodes to create icons like those of a car dashboard for the wearer to see. In another embodiment using alphanumeric characters, a scrolling message is displayed or a method like Rapid Serial Visual Presentation is completed to send more lengthy English text messages.

An eye-mountable device provides a notification signal to a wearer of the device when an eyelid of the wearer is closed. Because the eyelid is closed, the light signal displayed to the wearer does not have to compete with ambient light and be bright enough that a wearer of the device can see the light signal over ambient light. Accordingly, the power to be supplied to generate a light signal can be less than if a displayed signal needed to compete with ambient light.

An eye-mountable device that provides a notification signal to a wearer of the device when an eyelid is closed also offers a measure of privacy or discretion for the wearer. In other words, since an eyelid is closed when a light signal is displayed, the light signal is not broadcast to others that might be looking at the wearer at the time of the signal.

In one embodiment, an eye-mountable device is operable to receive feedback from a wearer such as message acknowledged, slower/faster, etc. One way a wearer provides such feedback is by moving the eyes to the left or right while the eyelid is closed. In one embodiment, an accelerometer separate from an eyelid sensor can be included in an eye-mountable device and connected to a controller associated with the device. Such accelerometer can sense a movement of the eyes left or right or up and down (e.g., rolling of eyes). The sensed movement of the eyes can be used to communicate (e.g., provide feedback) to the device. Such feedback can be, for example, a confirmation of a light signal based on one movement and a re-send light signal request based on another movement.

While embodiments of an eye-mountable device are useful for contact devices that incorporate sensing capabilities, other applications are also contemplated. For example, an eye-mountable device can provide a signal to a wearer of the device indicative of the state of the device itself, such as a battery charge level (e.g., a low charge level indicator) or a battery recharge reminder/indicator. In another embodiment related to accommodation, an eye-mountable device can provide a signal of a dynamic optic state of a lens such as whether a dynamic optic is powered on or off, or if on, an indication of, for example, near, intermediate or far correction. For example, an indicator may show a dynamic optic is unpowered (off) thus correcting distance vision; the dynamic optic is powered to correct at intermediate working distance; or the dynamic optic is powered to correct at near distances. A signal indicating correction for a left versus a right eye, respectively, may also be provided (e.g., left eye corrected for distance vision versus right eye corrected for near vision). Simple phone notifications could be sent to the contact lenses to display (e.g., alerting a wearer of a phone call or message). Sports performance information could be displayed (with the user rapidly blinking his eyes to see both the eyelid display and the physical world "at the same time"). In another embodiment, the system can be used as a visual alarm clock—waking a sleeper with a flashing light when he or she nods off while driving.

Figure 2A:
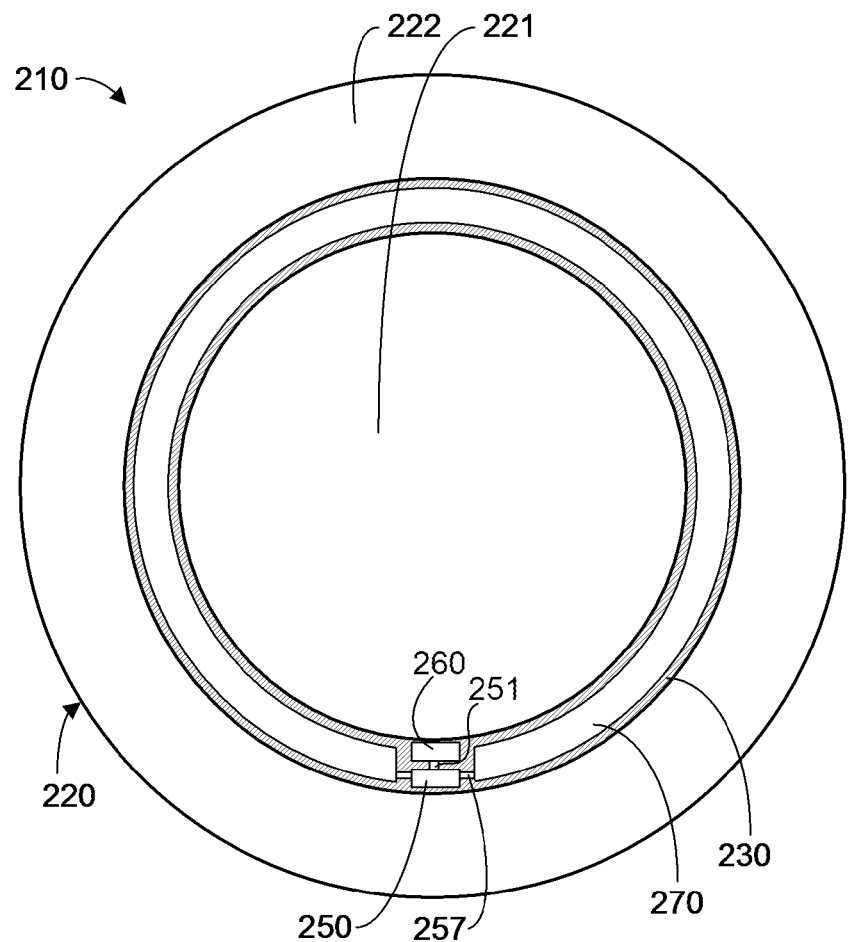
FIG. 2A is a top view of an example eye-mountable device described with references to FIG. 1.
Figure 2B:
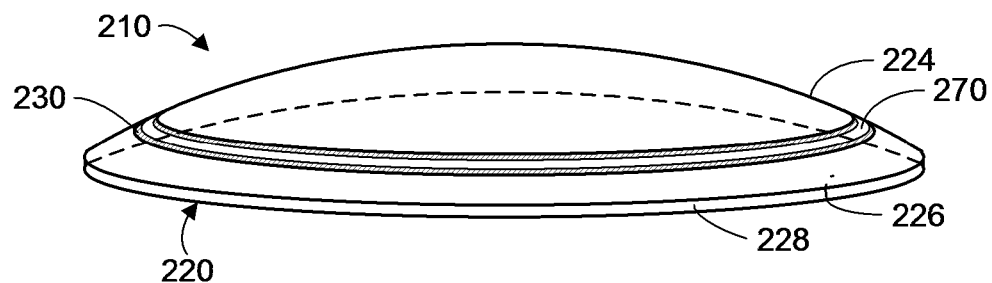
FIG. 2B is an aspect view of the example eye-mountable device shown in FIG. 2A.
Figure 2D:
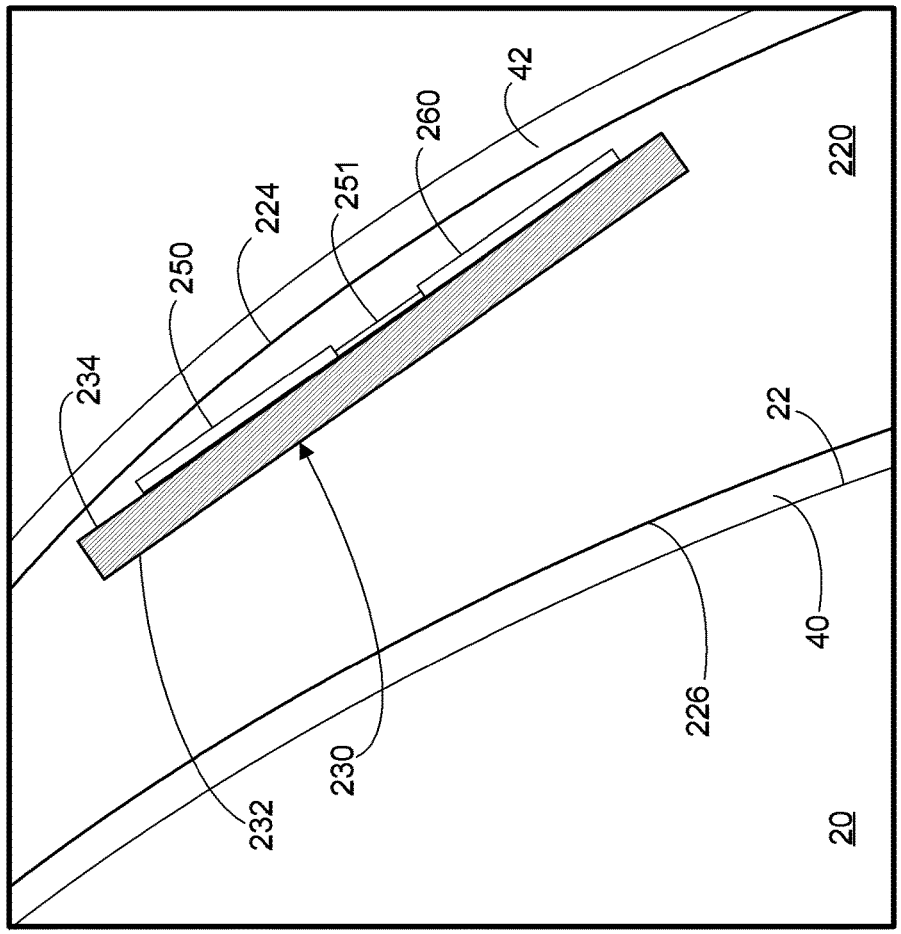
FIG. 2D is a side cross-section view enhanced to show the tear film layers surrounding the surfaces of the example eye-mountable device when mounted as shown in FIG. 2C.

FIGS. 1-2D describe in more detail an embodiment of an eye-mountable device or eye contact device including an eyelid sensor and a display for displaying a light signal along with having sensing capabilities to monitor blood glucose levels in a wearer. As noted above, it is appreciated that an eye-mountable device or eye contact device may include alternative or additional sensing capabilities or may have other capabilities. FIG. 1 is a block diagram of a system that includes an eye-mountable device or eye contact device including an eyelid sensor and a display for displaying a light signal. In this embodiment, the system is in wireless communication with an external reader. In another embodiment, a device need not be in communication with an external reader. Referring to FIG. 1, system 100 includes eye-mountable device 110. The exposed regions of eye-mountable device 110 are made of body 120 of a polymeric material formed to be contact-mounted to a corneal surface of an eye. Substrate 130 is embedded in body 120 to provide a mounting surface for power supply 140, controller 150, interactive electronics 160, and communication antenna 170. Interactive electronics 160 are operated by controller 150. Power supply 140 supplies operating voltages to controller 150 and/or interactive electronics 160. Antenna 170 is operated by controller 150 to, in one embodiment, communicate information to and/or from eye-mountable device 110. Antenna 170, controller 150, power supply 140, and interactive electronics 160 can all be situated on embedded substrate 130. Because eye-mountable device 110 includes electronics and is configured to be contact-mounted to an eye, it is also referred to herein as an ophthalmic electronics platform.

To facilitate contact-mounting, body 120 has a concave surface configured to adhere ("mount") to a moistened corneal surface (e.g., by capillary forces with a tear film coating the corneal surface). Additionally or alternatively, eye-mountable device 110 can be adhered by a vacuum force between the corneal surface and the polymeric material due to the concave curvature. While mounted with the concave surface against the eye, the outward-facing surface of body 120 can have a convex curvature that is formed to not interfere with eye-lid motion while eye-mountable device 110 is mounted to the eye. For example, body 120 can be a substantially transparent curved polymeric disk shaped similarly to a contact lens.

Body 120 can include one or more biocompatible materials, such as those employed for use in contact lenses or other ophthalmic applications involving direct contact with the corneal surface. Body 120 can optionally be formed in part from such biocompatible materials or can include an outer coating with such biocompatible materials. Body 120 can include materials configured to moisturize the corneal surface, such as hydrogels and the like. In some instances, body 120 can be a deformable ("non-rigid") material to enhance wearer comfort. In some instances, body 120 can be shaped to provide a predetermined, vision-correcting optical power, such as can be provided by a contact lens.

Substrate 130 includes one or more surfaces suitable for mounting interactive electronics 160, controller 150, power supply 140, and antenna 170. Substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on substrate 130 to form circuitry, electrodes, etc. For example, antenna 170 can be formed by depositing a pattern of gold or another conductive material on substrate 130. Similarly, interconnects 151, 157 between controller 150 and interactive electronics 160, and between controller 150 and antenna 170, respectively, can be formed by depositing suitable patterns of conductive materials on substrate 130. A combination of resists, masks, and deposition techniques can be employed to pattern materials on substrate 130. Substrate 130 can be a relatively rigid material, such as polyethylene terephthalate ("PET") or another material sufficient to structurally support the circuitry and/or electronics within body 120. Eye-mountable device 110 can alternatively be arranged with a group of unconnected substrates rather than a single substrate. For example, controller 150 and a bio-sensor or other bio-interactive electronic component can be mounted to one substrate, while antenna 170 is mounted to another substrate and the two can be electrically connected via interconnects 157.

In some embodiments, interactive electronics 160 (and substrate 130) can be positioned away from the center of eye-mountable device 110 and thereby avoid interference with light transmission to the eye through the center of eye-mountable device 110. For example, where eye-mountable device 110 is shaped as a concave-curved disk, substrate 130 can be embedded around the periphery (e.g., near the outer circumference) of the disk. In some embodiments, interactive electronics 160 (and substrate 130) can be positioned in the center region of eye-mountable device 110. Interactive electronics 160 and/or substrate 130 can be substantially transparent to incoming visible light to mitigate interference with light transmission to the eye.

In one embodiment, interactive electronics 160 includes eyelid sensor 163 that is operable to sense whether an eyelid of a wearer of eye-mountable device 110 is closed. Representative eyelid sensors include a sensor that is operable to detect a light change form a presence of light when an eye of a wearer of eye-mountable device 110 is open to an absence of light when an eyelid of a wearer of the device is closed. Examples of a light detecting sensor include a photocell (photoresistor), photodiode or phototransistor. A representative eyelid sensor alternatively or additionally can include a sensor that senses a movement, motion or travel of eye-mountable device 110. Generally speaking, a properly-fitted eye-mountable device such as a contact lens moves about one to three millimeters (mm) every time an eye blinks. Such movement of an eye-mountable device is thus indicative of a closing of the eyelids. An example of eyelid sensor that can detect a movement of eye-mountable device 110 is an accelerometer.

In addition to eyelid sensor 163, in one embodiment, interactive electronics 160 also includes display 164 such as a light emitting diode (LED) or an addressable pixel or pixel array that emits and/or transmits light to be perceived by the eye according to display instructions. Representatively, display 164 of interactive electronics 160 can optionally be positioned in the center of eye-mountable device 110 so as to generate perceivable visual cues (e.g., light signals, alphanumeric light signals) to a wearer of eye-mountable device 110.

In one embodiment, interactive electronics 160 includes feedback sensor 165 that is operable to sense a movement of the eyes to allow feedback with an eye-mountable device. Such feedback sensor 165 is, for example, an accelerometer that can sense a movement of an eye left or right or up or down. Detection or sensing of such movement can provide a signal to the device from a wearer of the device. An example signal may be representative of feedback from the wearer that it received a light signal from the device. In one embodiment, feedback sensor 165 is separate from eyelid sensor 163. In another embodiment, where eyelid sensor 163 is an accelerometer, feedback sensor 165 and eyelid sensor 163 may be the same accelerometer.

Substrate 130 can be shaped as a flattened ring with a radial width dimension sufficient to provide a mounting platform for the embedded electronics components. In one embodiment, substrate 130 has a thickness sufficiently small to allow substrate 130 to be embedded in body 120 without influencing the profile of eye-mountable device 110. Substrate 130 also has a thickness sufficiently large to provide structural stability suitable for supporting the electronics mounted thereon. For example, substrate 130 can be shaped as a ring with a diameter of about 10 millimeters, a radial width of about 1 millimeter (e.g., an outer radius 1 millimeter larger than an inner radius), and a thickness of about 50 micrometers. Substrate 130 can optionally be aligned with the curvature of the eye-mounting surface of eye-mountable device 110 (e.g., convex surface). For example, substrate 130 can be shaped along the surface of an imaginary cone between two circular segments that define an inner radius and an outer radius. In such an example, a surface of substrate 130 along the surface of the imaginary cone defines an inclined surface that is approximately aligned with the curvature of the eye mounting surface at that radius.

In one embodiment, power controller 150 and interactive electronics 160 are powered by a battery on the device. In another embodiment shown in FIG. 1, power supply 140 is operable to harvest ambient energy to power controller 150 and interactive electronics 160. For example, radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. Energy harvesting antenna 142 can optionally be a dual-purpose antenna that is also used to communicate information to external reader 180. That is, the functions of communication antenna 170 and energy harvesting antenna 142 can be accomplished with the same physical antenna. Still further, energy harvesting of an eye motion by a wearer of the device may be harvested as a power source. For example, energy produced by the blinking motion of a wearer can be captured.

Rectifier/regulator 146, in one embodiment, is used to condition the captured energy to a stable DC supply voltage 141 that is supplied to controller 150. For example, energy harvesting antenna 142 can receive incident radio frequency radiation. Varying electrical signals on the leads of antenna 142 are output to rectifier/regulator 146. Rectifier/regulator 146 rectifies the varying electrical signals to a DC voltage and regulates the rectified DC voltage to a level suitable for operating controller 150. Additionally or alternatively, output voltage from solar cell(s) 144 can be regulated to a level suitable for operating controller 150. Rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected to the output of rectifier 146 and configured to function as a low-pass filter.

Controller 150 is turned on when DC supply voltage 141 is provided to controller 150, and the logic in controller 150 operates interactive electronics 160 and antenna 170. Controller 150 can include logic circuitry configured to operate interactive electronics 160 so as to interact with a biological environment of eye-mountable device 110. The interaction could involve the use of one or more components, such analyte bio-sensor 162 in interactive electronics 160 to obtain input from the biological environment. Additionally or alternatively, the interaction could involve an interaction with eyelid sensor 163 to sense a closure of an eyelid of a wearer of eye-mountable device 110 and the use of one or more components, such as display 164, to provide an output (e.g., a light signal) to the biological environment (e.g., to display a light signal when an eyelid of a wearer of eye-mountable device 110 is closed or partially closed).

In one example, controller 150 includes sensor interface module 152 that is configured to operate analyte bio-sensor 162. Analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electrooxidized at the working electrode, which releases electrons to the working electrode, resulting in an amperometric current that can be measured through the working electrode.

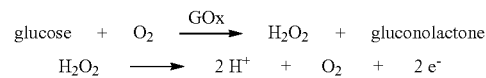

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

Controller 150 optionally includes display driver module 154 for operating display 164 to display a light signal. Display 164 can be an array of separately programmable light transmitting, light reflecting, and/or light emitting addressable pixels arranged in rows and columns. The individual pixel circuits can optionally include liquid crystal technologies, microelectromechanical technologies, emissive diode technologies (e.g., LEDs), etc. to selectively transmit, reflect, and/or emit light according to information from display driver module 154. Such a display can also optionally include more than one color of pixels (e.g., red, green, and blue pixels) to render visual content in color. Display driver module 154 can include, for example, one or more data lines providing programming information to the separately programmed pixels in display 164 and one or more addressing lines for setting groups of pixels to receive such programming information. Such display 164 situated on the eye can also include one or more lenses to direct light from the display to a focal plane perceivable by the eye.

Controller 150 can also include communication circuit 156 for sending and/or receiving information via antenna 170. Communication circuit 156 can optionally include one or more oscillators, mixers, frequency injectors, etc. to modulate and/or demodulate information on a carrier frequency to be transmitted and/or received by antenna 170. In some examples, eye-mountable device 110 is operable to indicate an output from a bio-sensor by modulating an impedance of antenna 170 in a manner that is perceivably by external reader 180. For example, communication circuit 156 can cause variations in the amplitude, phase, and/or frequency of backscatter radiation from antenna 170, and such variations can be detected by reader 180.

Controller 150 is connected to interactive electronics 160 via interconnects 151. For example, where controller 150 includes logic elements implemented in an integrated circuit to form sensor interface module 152 and/or display driver module 154, a patterned conductive material (e.g., gold, platinum, palladium, titanium, copper, aluminum, silver, metals, combinations of these, etc.) can connect a terminal on the chip to the interactive electronics 160. Similarly, controller 150 is connected to antenna 170 via interconnects 157.

It is noted that the block diagram shown in FIG. 1 is described in connection with functional modules for convenience in description. However, embodiments of eye-mountable device 110 can be arranged with one or more of the functional modules ("sub-systems") implemented in a single chip, integrated circuit, and/or physical feature. For example, while rectifier/regulator 146 is illustrated in power supply block 140, the rectifier/regulator 146 can be implemented in a chip that also includes the logic elements of controller 150 and/or other features of the embedded electronics in eye-mountable device 110. Thus, DC supply voltage 141 that is provided to controller 150 from power supply 140 can be a supply voltage that is provided on a chip by rectifier and/or regulator components the same chip. That is, the functional blocks in FIG. 1 shown as power supply block 140 and controller block 150 need not be implemented as separated modules. Moreover, one or more of the functional modules described in FIG. 1 can be implemented by separately packaged chips electrically connected to one another.

Additionally or alternatively, energy harvesting antenna 142 and communication antenna 170 can be implemented with the same physical antenna. For example, a loop antenna can both harvest incident radiation for power generation and communicate information via backscatter radiation.

External reader 180 includes antenna 188 (or group of more than one antennae) to send and receive wireless signals 171 to and from eye-mountable device 110. External reader 180 also includes a computing system with processor 186 in communication with memory 182. Memory 182 is a non-transitory computer-readable medium that can include, without limitation, magnetic disks, optical disks, organic memory, and/or any other volatile (e.g. RAM) or non-volatile (e.g. ROM) storage system readable by processor 186. Memory 182 can include data storage 183 to store indications of data, such as sensor readings (e.g., from analyte bio-sensor 162), program settings (e.g., to adjust behavior of eye-mountable device 110 and/or external reader 180), etc. Memory 182 can also include program instructions 184 that when executed by the processor 186 to cause the external reader 180 to perform processes specified by instructions 184. For example, program instructions 184 can cause external reader 180 to provide a user interface that allows for retrieving information communicated from eye-mountable device 110 (e.g., sensor outputs from analyte bio-sensor 162). External reader 180 can also include one or more hardware components for operating antenna 188 to send and receive wireless signals 171 to and from eye-mountable device 110. For example, oscillators, frequency injectors, encoders, decoders, amplifiers, filters, etc. can drive antenna 188 according to instructions from processor 186.

External reader 180 can be a smart phone, digital assistant, or other portable computing device with wireless connectivity sufficient to provide wireless communication link 171. External reader 180 can also be implemented as an antenna module that can be plugged in to a portable computing device, such as in an example where communication link 171 operates at carrier frequencies not commonly employed in portable computing devices.

In an example where eye-mountable device 110 includes analyte bio-sensor 162, system 100 can be operated to monitor the analyte concentration in tear film on the surface of the eye. Thus, eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

In one embodiment, to perform a reading with system 100 configured as a tear film analyte monitor, external reader 180 can emit radio frequency radiation 171 that is harvested to power eye-mountable device 110 via power supply 140. Radio frequency electrical signals captured by energy harvesting antenna 142 (and/or communication antenna 170) are rectified and/or regulated in rectifier/regulator 146 and regulated DC supply voltage 147 is provided to controller 150. Radio frequency radiation 171 thus turns on the electronic components within eye-mountable device 110. Once turned on, controller 150 operates analyte bio-sensor 162 to measure an analyte concentration level. For example, sensor interface module 152 can apply a voltage between a working electrode and a reference electrode in analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration.

In one embodiment, controller 150 associated with substrate 130 of eye-mountable device 110 includes memory 151 that is a non-transitory computer-readable medium that includes data storage operable to store program settings. In the embodiment where eye-mountable device 110 includes an analyte bio-sensor 162 operable to measure a glucose concentration, the program settings stored in memory 151 of controller 150 includes a threshold level or range of glucose concentration. Memory 151 also includes program instruction that when executed by controller 150 compares a measurement by analyte bio-sensor 162 to the threshold level or range. Additional program instructions included in memory 151 include instructions to be executed by controller 150 when a measured level is outside the threshold level or range. Representatively, such program instructions include gathering data from eyelid sensor 163 as to when an eyelid of a wearer of eye-mountable device 110 is closed and causing display driver module 154 to operate display 164 to emit a light signal when the eyelid is closed to alert the wearer that a glucose concentration is outside a threshold or range. Such alert can be in a signal light signal or provide information either in the form of a color of the light signal or an alphanumeric rating of the deviation from the threshold or range. Still further program instructions stored in memory 151 include instructions to be executed by controller 150 when the device receives feedback from a wearer (e.g., through a feedback sensor). One example of such instructions is the resending of a light signal if the feedback indicates a wearer did not receive a previously sent light signal.

Controller 150 can operate antenna 170 to communicate the sensor reading back to the external reader 180 (e.g., via communication circuit 156). The sensor reading can be communicated by, for example, modulating an impedance of communication antenna 170 such that the modulation in impedance is detected by external reader 180. The modulation in antenna impedance can be detected by, for example, backscatter radiation from antenna 170.

In some embodiments, system 100 can operate to non-continuously ("intermittently") supply energy to eye-mountable device 110 to power controller 150 and electronics 160. For example, radio frequency radiation 171 can be supplied to power eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from external reader 180 to eye-mountable device 110 to request a measurement. By periodically interrogating the eye-mountable device 110 (e.g., by supplying radio frequency radiation 171 to temporarily turn the device on) and storing the sensor results (e.g., via the data storage 183), external reader 180 can accumulate a set of analyte concentration measurements over time without continuously powering eye-mountable device 110.

FIG. 2A is a top view of an example of an eye-mountable electronic device (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device. Eye-mountable device 210 is formed of body 220 shaped as a curved disk. Body 220 can be a substantially transparent material to allow incident light to be transmitted to the eye while eye-mountable device 210 is mounted to the eye (worn). Body 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. Body 220 can be formed with one side having concave surface 226 suitable to fit over a corneal surface of an eye. The opposite side of body 220 can have convex surface 224 that does not interfere with eyelid motion while eye-mountable device 210 is mounted to the eye. Circular outer side edge 228 connects concave surface 224 and convex surface 226.

Eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 210 can be selected according to the size and/or shape of the corneal surface of the wearer's eye.

Body 220 can be formed with a curved shape in a variety of ways. For example, techniques similar to those employed to form vision-correction contact lenses, such as heat molding, injection molding, spin casting, etc. can be employed to form body 220. While eye-mountable device 210 is mounted in an eye (worn), convex surface 224 faces outward to the ambient environment while concave surface 226 faces inward, toward the corneal surface. Convex surface 224 can therefore be considered an outer, top surface of eye-mountable device 210 whereas concave surface 226 can be considered an inner, bottom surface. The "bottom" view shown in FIG. 2A is facing concave surface 226. From the bottom view shown in FIG. 2A, outer periphery 222, near the outer circumference of the curved disk is curved to extend out of the page, whereas central region 221, near the center of the disk is curved to extend into the page.

FIG. 2A and FIG. 2B show substrate 230 is embedded in body 220. The substrate 230 can be embedded to be situated along outer periphery 222 of body 220, away from central region 221. Substrate 230 generally does not interfere with vision because it is too close to the eye to be in focus and is positioned away from central region 221 where incident light is transmitted to the eye-sensing portions of the eye. Moreover, substrate 230 can be formed of a transparent material to further mitigate effects on visual perception.

Substrate 230 can be shaped as a flat, circular ring (e.g., a disk with a centered hole). The flat surface of substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. Substrate 230 and body 220 can be approximately cylindrically symmetric about a common central axis. Substrate 230 has, for example, a diameter of about 10 millimeters, a radial width of about 1 millimeter (e.g., an outer radius 1 millimeter greater than an inner radius), and a thickness of about 50 micrometers. Substrate 230 can be implemented in a variety of different form factors, similar to the discussion of substrate 130 in connection with FIG. 1 above.

Loop antenna 270, controller 250, and sensor electronics 260 are disposed on the embedded substrate 230. Controller 250 can be a chip including logic elements configured to operate sensor electronics 260 and loop antenna 270. Controller 250 is electrically connected to loop antenna 270 by interconnects 257 also situated on substrate 230. Similarly, controller 250 is electrically connected to sensor electronics 260 by interconnect 251. Interconnects 251, 257, loop antenna 270, and any conductive electrodes (e.g., for an electrochemical analyte sensor, etc.) can be formed from conductive materials patterned on substrate 230 by a process for precisely patterning such materials, such as deposition, photolithography, etc. The conductive materials patterned on substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of eye-mountable device 210, bio-interactive electronics module 260 is mounted to a side of substrate 230 facing the convex surface 224. Where bio-interactive electronics module 260 includes an eyelid sensor operable to determine when an eyelid of a wearer of eye-mountable device 210 is closed and, for example, an analyte bio-sensor. Mounting an analyte bio-sensor on substrate 230 to be close to convex surface 224 allows the bio-sensor to sense analyte concentrations in tear film 42 coating convex surface 224 of body 220 (e.g., a tear film layer distributed by eyelid motion). However, the electronics, electrodes, etc. situated on substrate 230 can be mounted to either the "inward" facing side (e.g., situated closest to concave surface 226) or the "outward" facing side (e.g., situated closest to convex surface 224). Moreover, in some embodiments, some electronic components can be mounted on one side of substrate 230, while other electronic components are mounted to the opposing side, and connections between the two can be made through conductive materials passing through substrate 230.

Loop antenna 270 is a layer of conductive material patterned along the flat surface of the substrate to form a flat conductive ring. In some examples, to allow additional flexibility along the curvature of the polymeric material, loop antenna 270 can include multiple substantially concentric sections electrically joined together. Each section can then flex independently along the concave/convex curvature of eye-mountable device 210. In some examples, loop antenna 270 can be formed without making a complete loop. For instances, antenna 270 can have a cutout to allow room for controller 250 and electronics module 260, as illustrated in FIG. 2A. However, loop antenna 270 can also be arranged as a continuous strip of conductive material that wraps entirely around the flat surface of substrate 230 one or more times. For example, a strip of conductive material with multiple windings can be patterned on the side of substrate 230 opposite controller 250 and electronics module 260. Interconnects between the ends of such a wound antenna (e.g., the antenna leads) can then be passed through substrate 230 to controller 250.

Figure 2C:
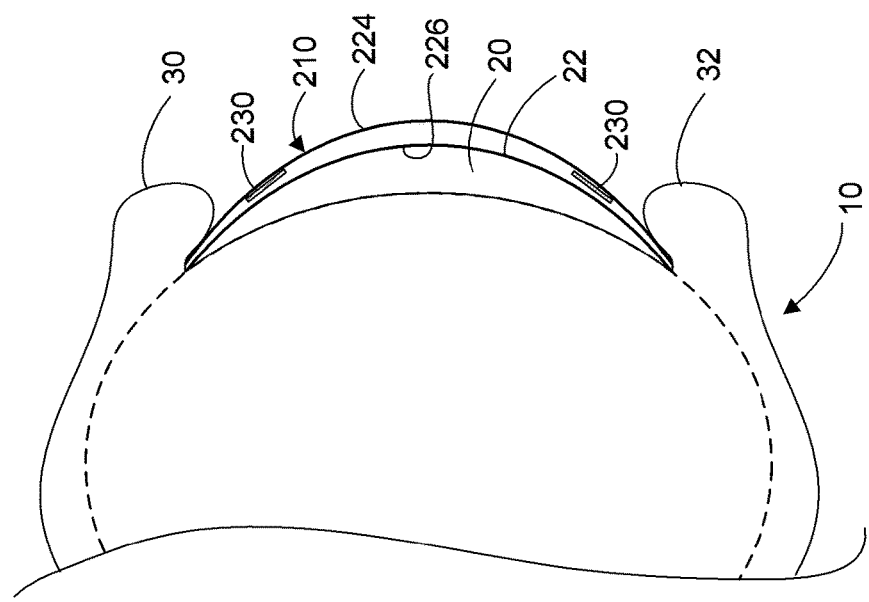
FIG. 2C is a side cross-section view of the example eye-mountable device shown in FIGS. 2A and 2B while mounted to a corneal surface of an eye.

FIG. 2C is a side cross-section view of eye-mountable electronic device 210 while mounted to corneal surface 22 of eye 10 of a wearer. FIG. 2D is a close-in side cross-section view enhanced to show electronics module 260 on eye-mountable device 210 when mounted as shown in FIG. 2C. As shown in FIG. 2D, while mounted to the corneal surface 22, tear film layers 40, 42 coat the concave surface 226 and convex surface 224. It is noted that the relative dimensions in FIG. 2C and FIG. 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

Eye 10 includes cornea 20 that is covered by bringing upper eyelid 30 and lower eyelid 32 together over the top of eye 10. Incident light is received by eye 10 through cornea 20, where light is optically directed to light sensing elements of eye 10 (e.g., rods and cones, etc.) to stimulate visual perception. The motion of eyelids 30, 32 distributes a tear film across the exposed corneal surface 22 of eye 10. The tear film is an aqueous solution secreted by the lacrimal gland to protect and lubricate eye 10. When eye-mountable device 210 is mounted in eye 10, the tear film coats both concave and convex surfaces 224, 226 with inner layer 40 (along concave surface 226) and outer layer 42 (along convex layer 224). Tear film layers 40, 42 can be about 10 micrometers in thickness and together account for about 10 microliters.

Tear film layers 40, 42 are distributed across corneal surface 22 and/or convex surface 224 by motion of eyelids 30, 32. For example, eyelids 30, 32 raise and lower, respectively, to spread a small volume of tear film across corneal surface 22 and/or convex surface 224 of eye-mountable device 210. Tear film layer 40 on corneal surface 22 also facilitates mounting eye-mountable device 210 by capillary forces between concave surface 226 and corneal surface 22. In some embodiments, eye-mountable device 210 can also be held over the eye in part by vacuum forces against corneal surface 22 due to the concave curvature of eye-facing concave surface 226.

As shown in the cross-sectional views in FIG. 2C and FIG. 2D, substrate 230 can be inclined such that the flat mounting surfaces of substrate 230 are approximately parallel to the adjacent portion of convex surface 224. As described above, substrate 230 is a flattened ring with inward-facing surface 232 (closer to concave surface 226 of body 220) and outward-facing surface 234 (closer to convex surface 224). Substrate 230 can have electronic components and/or patterned conductive materials mounted to either or both mounting surfaces 232, 234. As shown in FIG. 2D, electronics module 260, controller 250, and conductive interconnect 251 are mounted on outward-facing surface 234 such that electronics module 260 are relatively closer in proximity to convex surface 224 than if they were mounted on inward-facing surface 232.

With regard to an eyelid sensor as part of electronics module 260, the eyelid sensor is operable to sense or detect a closing of eyelids 30, 32. In one embodiment, the eyelid sensor senses a closing of eyelids 30, 32 by sensing a change in light on the sensor. An eyelid sensor such as a photocell can sense or detect light when eyelids 30, 32 are open but not when the eyelids are closed. In another embodiment, the eyelid sensor is operable to sense a movement of eye-mountable device 210. When eyelids 30, 32 close, such closure will generally cause a movement of eye-mountable device 210. Such movement can be detected by an eyelid sensor such as an accelerometer. Electronics module optionally further includes an interaction sensor that is operable to detect a movement of an eye of the wearer of the device allowing feedback between the device and the wearer.

Figure 3:
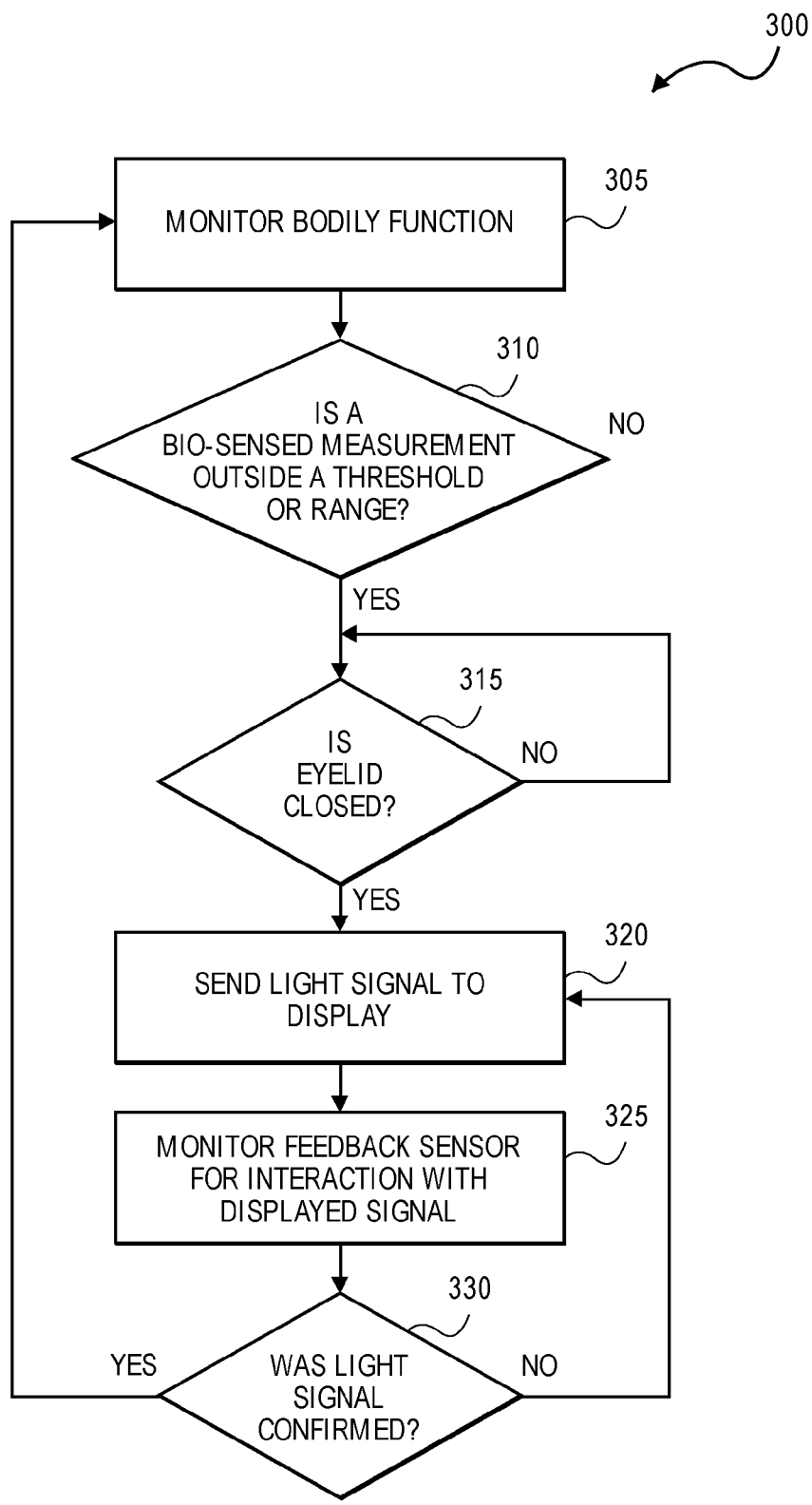
FIG. 3 is a flow chart of an embodiment of a method of analyzing a bio-sensed measurement and sending a light signal to a wearer of an eye-mountable device when an eyelid of the wearer is closed.

FIG. 3 shows a flow chart of a method that is employed by a controller associated with an eye-mountable device (e.g., controller 150, FIG. 1) according to machine-readable instructions provided thereto. In this embodiment, the eye-mountable device includes a bodily sensing capability to monitor a condition associated with a wearer of the device (e.g., a blood glucose level sensor). Referring to FIG. 3, in method 300, a controller monitors a bodily function such as a blood glucose level through the use of a sensor (block 305). The controller performs a comparison of monitored data with a threshold or range stored in an accessible memory and determines whether a measurement is outside the threshold or range (block 310). When it is determined that a measurement is outside a threshold or range, the method then proceeds to determine whether an eyelid of the wearer is closed (block 315). This determination may be a query by the controller to an eyelid sensor or by analyzing signals sent from the eyelid sensor to the controller. When it is determined that an eyelid is closed, the method directs the sending of a light signal to the display of the device (block 320).

In one embodiment, where an eye-mountable device includes a feedback sensor that measures eye movement to allow a wearer of the device to interact with the device, method 300 optionally includes an operation of monitoring a feedback sensor (e.g., a sensor that detects eye movement) for interaction with a displayed signal (block 325). In one embodiment, the interaction relates to feedback regarding whether a light signal sent to the display was seen by the wearer (block 330). If a light signal previously sent to the display of the device is confirmed, method 300 may return to monitoring of a bodily function (block 305). If a light signal is not confirmed by a wearer, the method resends the light signal (block 330) until a wearer confirms receipt.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Figure 5A:
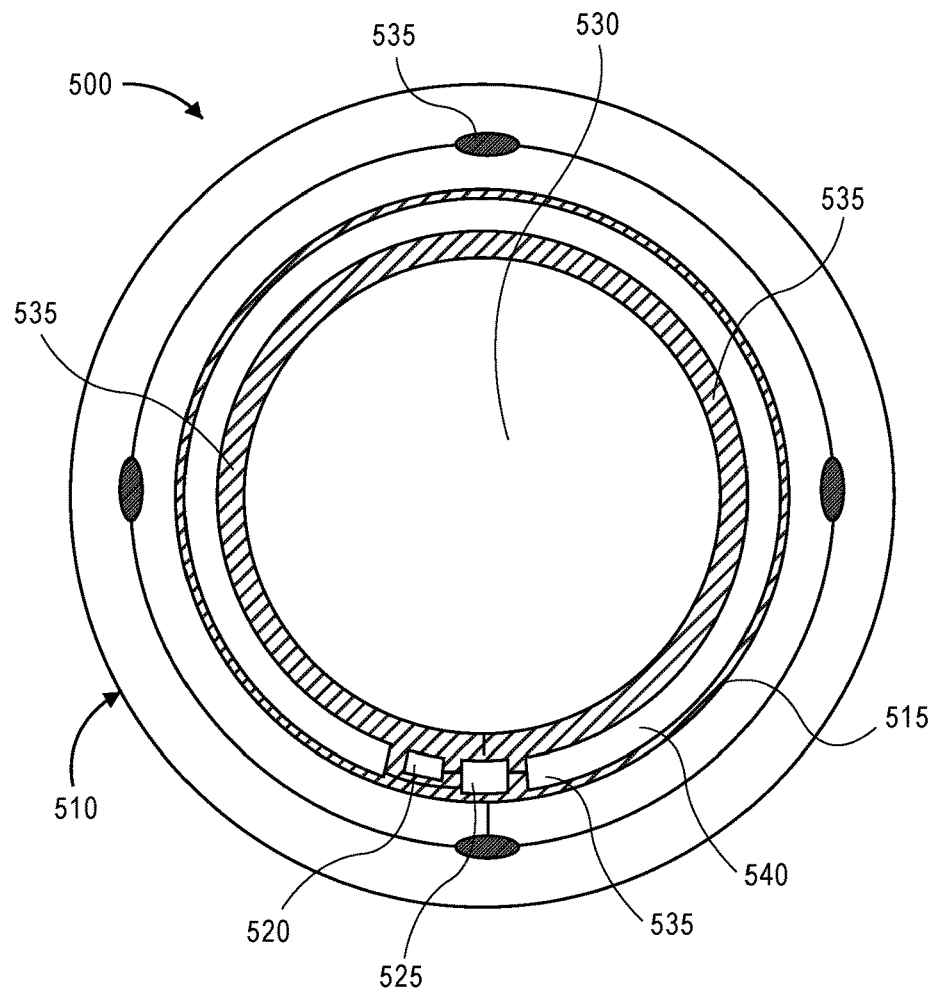
FIG. 5A is a top view of the eye-mountable device of FIG. 1, in accordance with an embodiment of the disclosure.
Figure 5B:
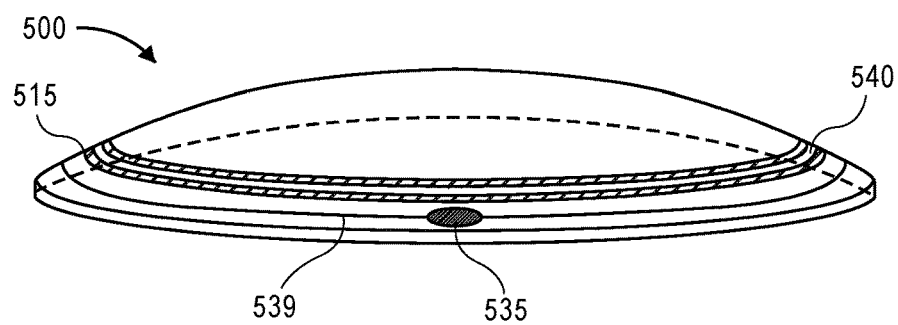
FIG. 5B is a perspective view of the eye-mountable device of FIG. 2A, in accordance with an embodiment of the disclosure.

In the above description with references to FIGS. 1-3, reference was drawn to an eye-mountable device including a bodily sensing capability to monitor a condition associated with a wearer of the devices (e.g., a blood glucose sensor). As noted, bodily sensing capability to monitor a condition is an example of a device where it could be beneficial to display a light signal to a wearer of the device when an eyelid of a wearer is closed. FIGS. 4 and 5A-5B present another example wear an eye-mountable device includes an accommodating lens. In this embodiment, an eyelid sensor system operable to detect when an eyelid of a wearer is closed includes one or more tear film sensors operable to measure an impedance of a current through a tear film (e.g., one or more pairs of tear film sensors). Representatively, an impedance of a current between a pair of tear film sensors may be correlated to a location of a contact lens in the eye and to a position of an eyelid (e.g., open or closed). A thickness of a tear film is non-uniform across the surface of an eye, and the impedance changes with respect to the thickness of the film: the thicker the film, the lower the impedance, the thinner the film the higher the impedance. Thus, a location of a lens and a position of an eyelid (e.g., open or closed) can be accurately determined relative to tear film reservoirs.

FIG. 4 is a functional block diagram of an embodiment of an eye-mountable device. In the depicted embodiment, eye-mountable device 400 includes an enclosure 410 formed to be contact-mounted to a corneal surface of an eye. Substrate 415 is embedded within or surrounded by enclosure 410 to provide a mounting surface for power supply 420, controller 425, antenna 440, and various interconnects 445 and 450. The illustrated embodiment of power supply 420 includes energy harvesting antenna 455, charging circuitry 460, and battery 465. The illustrated embodiment of controller 425 includes control logic 470, accommodation logic 475, and communication logic 480. As shown, accommodation actuator 430 and eyelid sensor system 435 are disposed in enclosure 410. Accommodation actuator 430 is connected to controller 425 to be electrically manipulated thereby. For example, accommodation actuator 430 may be characterized as a dynamic optic that may be a implemented with a liquid crystal cell that changes its index of refraction in response to an applied electrical bias signal. In other embodiments, accommodation actuator 430 may be implemented using other types of electro-active optical materials such as electro-optic materials that vary refractive index in the presence of an applied electric field or electro-mechanical structures that change the shape of a deformable lens. In one embodiment, controller 425 is operable to monitor a state of the eye-mountable device by receiving data or eliciting data from power supply 420, accommodation logic 475 and communication logic 480.

Similar to the embodiment described with reference to FIG. 1, enclosure 410 in eye-mountable device 400 is configured to be removably mounted over a cornea of an eye of a wearer, and has a size and shape that permits eyelid motion when enclosure 410 is mounted. In this embodiment, eyelid sensor system 435 includes one or more tear film sensors disposed within enclosure 410. The one or more tear film sensors are disposed to measure an impedance of a current through a tear film in an eye of a user, and to output a signal indicative of the impedance. Controller 425 is disposed within enclosure 410 and connected to eyelid sensor system 435 to receive the signal(s) and, in response to changes in the signal, actively control circuitry (e.g., accommodation actuator 430, antenna 440, power supply 420, etc.) disposed in eye-mountable device 400. In one embodiment, the one or more tear film sensors measure an impedance across a surface of eye-mountable device 400. In this embodiment, the impedance across the surface of eye-mountable device 100 is correlated with whether an eyelid of a wearer of the device is open or closed.

In addition to eyelid sensor system 435, in one embodiment, interactive electronics 463 also includes display 464 such as a light emitting diode (LED) or an addressable pixel or pixel array that emits and/or transmits light to be perceived by the eye according to display instructions. Representatively, display 464 of interactive electronics 460 can optionally be positioned in the center of eye-mountable device 400 so as to generate perceivable visual cues (e.g., light signals, alphanumeric light signals) to a wearer of eye-mountable device 400 when it is determined that an eyelid associated with the eye is closed. In response to data from the one or more tear film sensors (output data) that an eyelid is closed, controller 425 may send a signal to display 464 to display a light signal. Such light signal, in one embodiment, is indicative of a state of the device or the lens electronics of the device (e.g., power source charge (battery charge), state of dynamic optic (on/off; near, intermediate or far)). Data from the one or more tear film sensors may also be used to determine a gaze direction of a wearer and such data may be used by controller to manipulate accommodation actuator 430 to change an optical power of the lens.

In one embodiment, interactive electronics 463 includes feedback sensor 466 that is operable to sense a movement of the eyes to allow feedback with an eye-mountable device. Such feedback sensor 466 is, for example, an accelerometer that can sense a movement of an eye left or right or up or down. Detection or sensing of such movement can provide a signal to the device from a wearer of the device. An example signal may be representative of feedback from the wearer that it received a light signal from the device or that an optical power of the lens should be changed.

Power supply 420 supplies operating voltages to controller 425 and/or accommodation actuator 430. Antenna 440 is operated by controller 425 to communicate information to and/or from eye-mountable device 400. In the illustrated embodiment, antenna 440, controller 425, and power supply 420 are disposed on/in substrate 415, while eyelid sensor system 435, interactive electronics 463 and accommodation actuator 430 are disposed in enclosure 410 (not in/on substrate 415). However, in other embodiments, the various pieces of circuitry and devices contained in eye-mountable device 400 may be disposed in/on substrate 415 or in enclosure 410, depending on the specific design of eye-mountable device 400. For example, in one embodiment, accommodation actuator 430 may be disposed on a transparent substrate.

Similar to the embodiment described above with reference to FIG. 1, substrate 415 includes one or more surfaces suitable for mounting controller 425, power supply 420, and antenna 440. Substrate 415 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 415 to form circuitry, electrodes, etc. Substrate 415 can be a relatively rigid material, such as polyethylene terephthalate ("PET") or another material sufficient to structurally support the circuitry and/or electronics within enclosure 410. Eye-mountable device 400 can alternatively be arranged with a group of unconnected substrates rather than a single substrate 415. Substrate 415 may also be a continuous piece of semiconductor, housing all or some of the aforementioned pieces of device architecture as integrated circuitry.

In one embodiment, substrate 415 is shaped as a flattened ring with a radial width dimension sufficient to provide a mounting platform for the embedded electronic components. Substrate 415 can have a thickness sufficiently small to allow substrate 415 to be embedded in enclosure 410 without adversely influencing the profile of eye-mountable device 400 and a thickness sufficiently large to provide structural stability suitable for supporting the electronics mounted on it. For example, substrate 415 can be shaped as a ring with a diameter of about 10 millimeters, a radial width of about 1 millimeter (e.g., an outer radius 1 millimeter larger than an inner radius), and a thickness of about 50 micrometers. Substrate 415 can optionally be aligned with the curvature of the eye-mounting surface of eye-mountable device 400 (e.g., convex surface). For example, substrate 415 can be shaped along the surface of an imaginary cone between two circular segments that define an inner radius and an outer radius. In such an example, the surface of substrate 415 along the surface of the imaginary cone defines an inclined surface that is approximately aligned with the curvature of the eye-mounting surface at that radius.

In the illustrated embodiment, power supply 420 includes battery 465 to power the various embedded electronics, including controller 425. Battery 465 may be inductively charged by charging circuitry 460 and energy harvesting antenna 455. In one embodiment, antenna 440 and energy harvesting antenna 455 are independent antennae, which serve their respective functions of energy harvesting and communications. In another embodiment, energy harvesting antenna 455 and antenna 440 are the same physical antenna that are time shared for their respective functions of inductive charging and wireless communications with reader 405.

Controller 425 contains logic to choreograph the operation of the other embedded components. Control logic 470 controls the general operation of eye-mountable device 400, including providing a logical user interface, power control functionality, etc. Accommodation logic 475 includes logic for receiving signals from sensors monitoring the orientation of the eye, determining the current gaze direction, or focal distance of the user and manipulating accommodation actuator 430 (focal distance of the contact lens) in response to these physical cues. The accommodation can be implemented in real-time based upon feedback from gaze tracking, or permit the user to select specific accommodation regimes (e.g., near-field accommodation for reading, far-field accommodation for regular activities, etc.). Communication logic 480 provides communication protocols for wireless communication with reader 405 via antenna 440. Controller 425 optionally includes display driver module 454 for operating display 464 to display a light signal. The various logic modules of controller 425 may be implemented in software/firmware executed on a general purpose microprocessor, in hardware (e.g., application specific integrated circuit), or a combination of both.

The illustrated embodiment also includes reader 405 with processor 482, antenna 484 and memory 486. Memory 486 in reader 405 includes data storage 488 and program instructions 490. As shown reader 405 may be disposed outside of eye-mountable device 400, but may be placed in its proximity to charge eye-mountable device 400, send instructions to eye-mountable device 400, and/or extract data from eye-mountable device 400. In one embodiment, reader 405 may resemble a conventional contact lens holder that the user places eye-mountable device 400 in at night to charge, extract data, clean the lens, etc.

External reader 405 includes an antenna 484 (or group of more than one antennae) to send and receive wireless signals 471 to and from eye-mountable device 400. External reader 405 also includes a computing system with a processor 482 in communication with a memory 486. Memory 486 is a non-transitory computer-readable medium that can include, without limitation, magnetic disks, optical disks, organic memory, and/or any other volatile (e.g., RAM) or non-volatile (e.g., ROM) storage system readable by the processor 482. Memory 486 can include a data storage 488 to store indications of data, such as data logs (e.g., user logs), program settings (e.g., to adjust behavior of eye-mountable device 400 and/or external reader 405), etc. Memory 486 can also include program instructions 490 for execution by processor 482 to cause the external reader 405 to perform processes specified by program instructions 490. For example, program instructions 490 can cause external reader 405 to provide a user interface that allows for retrieving information communicated from eye-mountable device 400 or allows transmitting information to eye-mountable device 400 to program or otherwise select operational modes of eye-mountable device 400. External reader 405 can also include one or more hardware components for operating antenna 484 to send and receive wireless signals 471 to and from eye-mountable device 400.

External reader 405 can be a smart phone, digital assistant, or other portable computing device with wireless connectivity sufficient to provide wireless communication link 471. External reader 405 can also be implemented as an antenna module that can be plugged in to a portable computing device, such as in an embodiment where communication link 471 operates at carrier frequencies not commonly employed in portable computing devices. In some instances, external reader 405 is a special-purpose device configured to be worn relatively near a wearer's eye to allow wireless communication link 471 to operate with a low power budget.

For example, external reader 405 can be integrated in a piece of jewelry such as a necklace, earring, etc. or integrated in an article of clothing worn near the head, such as a hat, headband, etc.

FIG. 5A is a top view of eye-mountable device 500 (which is an embodiment of eye-mountable device 100 of FIG. 4). The illustrated embodiment of eye-mountable device 500 includes: enclosure 510, substrate 515, power supply 520, controller 525, accommodation actuator 530, eyelid sensor system (including individual tear film sensors 535), interconnects 539 and antenna 540. It should be appreciated that FIGS. 5A and 5B are not necessarily drawn to scale, but have been illustrated for purposes of explanation only in describing the arrangement of example eye-mountable device 500.

Eye-mountable device 500 is a circular contact lens with an eyelid sensor system including one or more tear film sensors 535. The eyelid sensor system is disposed within eye-mountable device 500 and connected to output a signal in response to a change in tear film thickness in an eye of the user. Accommodation actuator 530 is circular and disposed in eye-mountable device 500 to optically align with a cornea of the user when eye-mountable device 500 is mounted in an eye of the user. In one embodiment, the one or more tear film sensors 535 are disposed around a periphery of eye-mountable device 500 such that light entering the eye of the user is substantially unobstructed by the one or more tear film sensors 535 when enclosure 510 is mounted over the cornea. In the depicted embodiment, eyelid sensor system includes at least two tear film sensors 535, and measures the impedance between the at least two tear film sensors 535 disposed on opposite sides of eye-mountable device 500. In the illustrated embodiment, tear film sensors 535 are exposed electrodes which may include metal or conductive polymer. Controller 525 is disposed in eye-mountable device 500 and electrically connected to the eyelid sensor system and accommodation actuator 530. Controller 525 includes logic that when executed by controller 525 causes controller 525 to perform operations including: (1) controlling one or more other pieces of circuitry disposed in eye-mountable device 500 in response to the signal from the eyelid sensor system; and (2) electrically manipulating accommodation actuator 530 to change an optical power of the contact lens.

In the depicted embodiment, interconnects 539 extend between one or more tear film sensors 535 and may include many small wires to individually transmit signals from one or more tear film sensors 535 to controller 525. Power supply 520 is also coupled to controller 525, accommodation actuator 530, and antenna 540 to supply power to controller 525, supply power to accommodation actuator 530, and/or receive power from antenna 540.

FIG. 5B is a perspective view of eye-mountable device 500 of FIG. 5A, in accordance with an embodiment of the disclosure. Enclosure 510 of eye-mountable device 500 is shaped as a curved disk. As shown, to facilitate contact-mounting, enclosure 510 can have a concave surface configured to adhere ("mount") to a moistened corneal surface (e.g., by capillary forces with a tear film coating the corneal surface). Additionally, eye-mountable device 500 may be adhered by a vacuum force between the corneal surface and enclosure 510 due to the concave curvature. While mounted with the concave surface against the eye, the outward-facing surface of enclosure 510 can have a convex curvature that is formed to not interfere with eye-lid motion while eye-mountable device 500 is mounted to the eye.

Similar to the embodiment described with references to FIGS. 2A and 2B, enclosure 510 may be a substantially transparent material to allow incident light to be transmitted to the eye while eye-mountable device 500 is mounted to the eye. Enclosure 510 may be a biocompatible material similar to those employed to form vision correction and/or cosmetic contact lenses in optometry, such as a polymeric material like polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate) combinations of these, or otherwise.

In one embodiment described with reference to FIG. 4 and FIGS. 5A-5B, the eyelid sensor system applies an alternate current (AC) voltage across the surface of the device and measures an impedance across the eye-mountable device. The impedance is proportional to a tear film thickness. With reference to FIG. 5A, the AC waveform is representatively applied from right tear film sensor 535 to left tear film sensor 535 and/or from top tear film sensor 535 to bottom tear film sensor 535. This electric field distribution may provide information about the position of the eye as well as the position of the eyelid.

When the eyelid of a wearer is closed, the impedance measured between tear film sensors 535 may be very low because the tear film sensors are submerged in a thick layer of tear film under the eyelids. When the eyelid opens, the impedance may increase rapidly because the tear film sensors have a much thinner tear film layer covering them, decreasing the volumetric conduction path between tear film sensors. When the eyes squint, the impedance may drop again (but not as far as when the eyes are closed) because of the increased volumetric conduction path through the tear film between the tear film sensors. Since the impedance value is lowest when the eyelid is closed, this information can be used to direct the sending of a light signal to a display of the device (e.g., display 464, FIG. 4).

In the embodiment described with reference to FIGS. 4 and 5A-5B information about the position of an eyelid is derived from an eyelid sensor system that measured impedance changes using tear film sensors 535. In another embodiment, the position of an eyelid is measured by capacitance changes. In this embodiment, tear film sensors 535 are capacitance sensors that sense eyelid overlap in a manner similar to capacitive touch screens. As an eyelid covers different portions of a sensor, the capacitance changes which can be measured. By monitoring the amount and position of eyelid overlap, feedback signals from the capacitance sensors can be measured by controller 525 to determine when an eyelid is closed. In another embodiment, an eyelid sensor system includes a combination of tear film sensors and capacitance sensors that collectively may be used to determine when an eyelid is closed.

The above description of illustrated embodiments, including what is described in the Abstract, is not intended to be exhaustive or to limit the claims to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-mountable device comprising:
   a lens comprising a polymeric material, the lens operable to be removably mounted over an eye and to be compatible with a motion of an eyelid when a concave surface of the lens is so mounted;
   an eyelid sensor disposed in or on the lens and operable to provide output data indicative of whether the eyelid of the eye on which the lens is mounted is closed;
   a display disposed in or on the lens and operable to display a light signal in response to the output data from the eyelid sensor indicating that the eyelid is closed;
   a feedback sensor disposed in or on the lens to sense a feedback from a wearer of the eye-mountable device and output a feedback signal; and
   a control electronics coupled to the display and the feedback sensor, the control electronics configured to cause the display to repeat displaying the light signal when the eyelid is closed unless the feedback signal indicates an acknowledgement that the light signal was noticed by the wearer.

2. The eye-mountable device of claim 1, wherein the eyelid sensor is operable to detect a light change.

3. The eye-mountable device of claim 2, wherein the eyelid sensor comprises a photocell.

4. The eye-mountable device of claim 1, wherein the eyelid sensor is operable to detect a movement of the lens.

5. The eye-mountable device of claim 1, wherein the feedback sensor comprises an accelerometer and wherein the control electronics are configured to identify an eye motion as the acknowledgement.

6. The eye-mountable device of claim 1, further comprising a power supply coupled to the lens and operable to power a light signal displayed on the display.

7. The eye-mountable device of claim 1, wherein the eyelid sensor comprises an impedance sensor configured to measure an impedance across the lens that changes dependent upon whether the eyelid is open or closed.

8. The eye-mountable device of claim 1, wherein the control electronics are further coupled to monitor a state of the device and the light signal indicates the monitored state.

9. The eye-mountable device of claim 8, further comprising:
   a power source, wherein the monitored state is a charge of the power source.

10. The eye-mountable device of claim 8, further comprising:
    a dynamic optic, wherein the monitored state is an accommodation state of the dynamic optic and the light signal indicates the accommodation state of the dynamic optic.

11. The eye-mountable device of claim 1, wherein the control electronics are further coupled to monitor a bodily condition and the light signal indicates the bodily condition.

12. The eye-mountable device of claim 11, wherein the light signal comprises a series of light signals.

13. The eye-mountable device of claim 1, wherein the feedback sensor is operable to sense a movement of the eye.

14. The eye-mountable device of claim 13, wherein the control electronics are configured to recognize a left and right movement of the eye or an up and down movement of the eye as the acknowledgement.

15. A machine-readable medium that stores instructions that, when executed by an eye-mountable device, will cause the eye-mountable device to perform operations comprising:
    monitoring an impedance across the eye-mountable device from one or more sensors peripherally disposed about the eye-mountable device, the impedance changing dependent upon whether an eyelid of a wearer of the eye-mountable device is open or closed;
    determining whether the eyelid of the wearer of the eye-mountable device is closed based upon the impedance; and
    when the eyelid of the wearer is determined to be closed, emitting a light signal optically with photons from the eye-mountable device.

16. The machine-readable medium of claim 15, wherein the light signal is indicative of a bodily condition.

17. The machine-readable medium of claim 16, wherein the light signal comprises a first signal indicative of the bodily condition in a first state and a different second signal indicative of the bodily condition in a second state that is different from the first state.

18. The machine-readable medium of claim 15, wherein the light signal is indicative of a state of the eye-mountable device.

19. The machine-readable medium of claim 18, wherein the state of the eye-mountable device is a power source charge.

20. The machine-readable medium of claim 15, wherein the eye-mountable device comprises a dynamic optic and the light signal is indicative of a state of the dynamic optic.

21. The machine-readable medium of claim 15, further comprising:
    repeating emission of the light signal when the eyelid is closed unless an acknowledgement indicating that the light signal was noticed by a user is received.

* * * * *